(12) United States Patent
Matayoshi

(10) Patent No.: US 8,053,409 B2
(45) Date of Patent: *Nov. 8, 2011

(54) AGENT FOR PROPHYLAXIS OF REFLEX SYMPATHETIC DYSTROPHY AFTER CEREBRAL APOPLEXY

(75) Inventor: Satoru Matayoshi, Naha (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/030,494

(22) Filed: Feb. 18, 2011

(65) Prior Publication Data

US 2011/0144018 A1    Jun. 16, 2011

Related U.S. Application Data

(63) Continuation of application No. 11/905,082, filed on Sep. 27, 2007, now Pat. No. 7,919,460.

(60) Provisional application No. 60/827,445, filed on Sep. 29, 2006.

(30) Foreign Application Priority Data

Sep. 27, 2006    (JP) .................................. 2006-261686

(51) Int. Cl.
*A61K 38/23*    (2006.01)
(52) U.S. Cl. ...................................................... 514/11.9
(58) Field of Classification Search .................... None
See application file for complete search history.

(56) References Cited

U.S. PATENT DOCUMENTS

2007/0015702 A1    1/2007    Ito et al.

OTHER PUBLICATIONS

Appelboom, T., "Calcitonin in Reflex Sympathetic Dystrophy Syndrome and Other Painful Conditions," Bone, vol. 30, No. 5, Supplement, pp. 84S-86S, May 2002.
Australian Office Action dated Apr. 30, 2010 for Australian Application No. 2007301170.
Braus et al., "The shoulder-hand syndrome after stoke: a prospective clinical trial", Ann. Neruol., vol. 36, 1994, pp. 728-733.
Buckle, R., "P18. The Effect of Calcitonin in Sudeck's Atrophy," Abstracts from the Bone and Tooth Society Meeting, p. 480, Apr. 1989.
Canadian Application No. 2,664,300, Office Action, Oct. 7, 2010, pp. 1-3.
Casale et al., "Increased sympathetic tone in the left arm of patients affected by symptomatic myocardial ischemia", Functional Neruology, vol. 4, 1989, pp. 161-163.
Daoudi et al., "A comparative study of two calcitonins in the prevention of post-traumatic reflex sympathetic dystrophy", J. Pharm. Clin., vol. 11, 1992, pp. 95-100.
Daviet et al., "Clinical factors in the prognosis of complex regional pain syndrome type I after stroke: a prospective study", Am. J. Phys. Med. Rehabil., vol. 81, 2002, pp. 34-39.
Gobelet et al., "The Effect of Adding Calcitonin to Physical Treatment on Reflex Sympathetic Dystrophy," Pain, vol. 48, pp. 171-175, 1992.
Hamamci et al., "Calcitonin Treatment in Reflex Sympathetic Dystrophy: A Preliminary Study," British Journal of Clinical Practice, vol. 50, No. 7, Oct./Nov. 1996, pp. 373-375.
Ide et al., "Pathological condition and treatment for reflex sympathetic dystrophy—focusing on shoulder-hand syndrome", J. Jpn. Orthop. Assoc., vol. 69, Nos. 2 & 3, 1995.
International Preliminary Report on Patentability and Written Opinion of the International Searching Authority mailed Apr. 9, 2009 for International Application No. PCT/JP2007/068618.
Kissling et al., "Prevention of recurrence of Sudeck's disease with calcitonin", Rev. Chir. Orthop. Reparatrice Appar. Mot., vol. 77, 1991, pp. 562-567.
Kondo et al., "Protocol to prevent shoulder-hand syndrome after stroke", Arch. Phys. Med. Rehabil., vol. 82, 2001, pp. 1619-1623.
Korean Application No. 10-2008-7031433; Korean Office Action; Dec. 3, 2010; pp. 1-5.
Marx et al., "Preventing recurrence of reflex sympathetic dystrophy in patients requiring an operative intervention at the site of dystrophy after surgery", Clin. Rheumatol., vol. 20, 2001, pp. 114-118.
Partial English Translation of the Relevant Parts of Yamaga et al., "Nosocchu Henmahi ni Tomonau Itami Katate Shokogun" (Special edition, Pain Accompanying Post-Stroke Hemiplegia—Shoulder-hand Syndrome), Journal of Pain and Clinical Medicine, vol. 4, No. 2, pp. 115-122, 2004.
Phillippe Gallien et al., "The reflex sympathetic dystrophy syndrome in patients who have had a spinal cord injury," Paraplegia, vol. 33, Dec. 1995, pp. 715-720.
Quatraro, "Calcitonin in painful diabetic neuropathy", Lancet, vol. 339, 1992, pp. 746-747.
R. Nuti et al., "Carbocalcitonin Treatment in Sudeck's Atrophy," Clinical Orthop., No. 215, Feb. 1987, pp. 217-222.
Riou et al., "Can algodystrophy be prevented by thyrocalcitonin?", Rev. Chir. Orthop. Reparatrice Appar. Mot., vol. 77, 1991, pp. 208-210.
Siligardi et al., Correlations between biological activities and conformational properties for human, salmon, eel, porcine calcitonins and Elcatonin elucidated by CD spectroscopy. Eur J Biochem. May 1, 1994;221(3):1117-25.

(Continued)

*Primary Examiner* — Daniel E Kolker
*Assistant Examiner* — Gregory S Emch
(74) *Attorney, Agent, or Firm* — Birch Stewart Kolasch & Birch LLP

(57) ABSTRACT

The present invention is intended to provide a novel pharmaceutical agent having an excellent preventive effect on post-stroke RSD. The present invention provides an agent for preventing the onset of post-stroke RSD, comprising natural calcitonin or a calcitonin derivative as an active ingredient. The present invention is also intended to provide a method for preventing the onset of post-stroke RSD, comprising administering natural calcitonin or a calcitonin derivative and use of natural calcitonin or a calcitonin derivative for producing an agent for preventing the onset of post-stroke RSD.

14 Claims, No Drawings

OTHER PUBLICATIONS

Terayama, "Apporach to the pain in orthopedics 5 Shoulder Pain", 1998, pp. 183-197.

Wade et al., "A critical review of controlled clinical trials for peripheral neruopathic pain and complex regional pain syndromes", Pain, USA, vol. 73, 1997, pp. 123-139.

Yamaga et al., "Special edition, diagnosis and treatment of reflex sympathetic dystrophy (RSD) Drug therapy for reflex sympathetic dystrophy (RSD)—Calcitonin treatment as main therapy", vol. 9, 1996, pp. 1191-1198.

Yamaga et al., "Special edition, pain accompanying post-stroke hemiplegia Shoulder-hand syndrome", vol. 4, No. 2, 2004, pp. 115-122.

Yamaga et al., "Special edition, reflex sympathetic dystrophy Treatment for reflex sympathetic dystrophy—from an orthopedic perspective", vol. 54, 2001, pp. 306-314.

Zollinger et al., "Effect of vitamin C on frequency of reflex sympathetic dystrophy in wrist fractures: a randomized trial", Lancet, vol. 354, 1999, pp. 2025-2028.

AGENT FOR PROPHYLAXIS OF REFLEX SYMPATHETIC DYSTROPHY AFTER CEREBRAL APOPLEXY

CROSS REFERENCE TO RELATED APPLICATION

This application is a Continuation of application Ser. No. 11/905,082, filed on Sep. 27, 2007, now U.S. Pat. No. 7,919,460 which claims priority to U.S. Provisional Application No. 60/827,445, filed on Sep. 29, 2006, the entire contents of which are hereby incorporated by reference into the present application and for which priority is claimed under 35 U.S.C. §120.

BACKGROUND OF THE INVENTION

1. Field of the Invention

The present invention relates to a pharmaceutical agent comprising, as an active ingredient, natural calcitonin or a calcitonin derivative having a preventive effect on the onset of reflex sympathetic dystrophy developed after stroke.

2. Description of the Related Art

Reflex sympathetic dystrophy (hereinafter, also abbreviated to RSD) is a disease that is characterized by clinical symptoms such as pain, hyperalgesia, motor dysfunction, and dysautonomia and mainly triggered and developed by a limb trauma or surgical invasion. This disease is also frequently triggered and developed by a vascular disease in the trunk of the body, such as stroke or myocardial infarction. The post-stroke or post-myocardial infraction RSD is often developed as shoulder-hand syndrome (Ishibashi T., "Reflex sympathetic dystrophy", Orthopedics—Approach to pain—5, Shoulder pain (supervised by Terayama K. and Kataoka O.), 183-197, 1998, Nankodo Co., Ltd.).

The shoulder-hand syndrome, which is a kind of RSD, causes RSD symptoms in a region spreading from the shoulder joint to the hand. Specifically, in many cases of RSD, shoulder pain occurs at first and pain and stiffness of fingers on flexion, swelling of the back of the hand, and hidrosis of the palm concur with or follow the shoulder pain (Ishibashi T., "Reflex sympathetic dystrophy", Orthopedics—Approach to pain—5, Shoulder pain (supervised by Terayama K. and Kataoka O.), 183-197, 1998, Nankodo Co., Ltd.). Restrictions on person's movement in the upper limb caused by severe pain not only serve as a major hindrance factor for rehabilitation for overcoming paralysis associated with stroke or myocardial infraction but also have serious consequences to the QOL (quality of life) and ADL (activities of daily living) of patients (Yamaga M. et al., "Shoulder-hand syndrome", Journal of pain and clinical medicine, 4 (2), 115-122, 2004). According to an epidemiological investigation, 10 to 20% of myocardial infraction patients (Ishibashi T., "Reflex sympathetic dystrophy", Orthopedics—Approach to pain—5, Shoulder pain (supervised by Terayama K. and Kataoka O.), 183-197, 1998, Nankodo Co., Ltd. and Casale R. et al.: Increased sympathetic tone in the left arm of patients affected by symptomatic myocardial ischemia., Funct. Neurol., 4, 161-163, 1989.) and 23 to 70% of stroke patients (Daviet J C. et al.: Clinical factors in the prognosis of complex regional pain syndrome type I after stroke: a prospective study., Am. J. Phys. Med. Rehabil., 81, 34-39, 2002.) develop such shoulder-hand syndrome. This disease is resistant to therapy and leaves severe residual disabilities in many cases. Moreover, the disease tends to recur even when it is once remitted (Ishibashi T., "Reflex sympathetic dystrophy", Orthopedics—Approach to pain—5, Shoulder pain (supervised by Terayama K. and Kataoka O.), 183-197, 1998, Nankodo Co., Ltd.).

Various therapeutic methods for RSD or shoulder-hand syndrome have been reported so far. However, a systematic therapeutic method remains to be established (Yamaga M. et al., "Shoulder-hand syndrome", Journal of pain and clinical medicine, 4 (2), 115-122, 2004 and Yamaga M. et al., "Treatment of reflex sympathetic dystrophy", Neurological Medicine, 54, 306-314, 2001). For example, low-dose steroid has been used on a clinical site and however, is restricted to short-time use for the purpose of circumventing various side effects (increased susceptibility to infection, bone density loss, abnormal glucose metabolism, stomach ulcer, etc.) attributed to the long-term administration of steroid. Thus, the long-term control of the disease is allegedly difficult. Another therapeutic method that is preferably performed is a nerve block in which local anesthesia is repetitively performed to sympathetic nerves. However, this method had many such problems that: tissues at the injection site adhere to each other and make a surgical operation difficult, if this site needs the surgical operation in the future; and the method has the risk of hematoma formation attributed to the block during treatment using drugs having an anticoagulant effect, such as ameliorants of cerebral circulation or thrombolytic agents.

Thus, RSD is exceedingly difficult to treat, once developed. Therefore, it is important to prevent the onset itself of RSD under the present circumstances.

For RSD triggered and developed by a trauma or surgical invasion, the preventive effect of vitamin C on the initial onset thereof (Zollinger P E. et al.: Effect of vitamin C on frequency of reflex sympathetic dystrophy in wrist fractures: a randomized trial., Lancet, 354, 2025-2028, 1999.) and the preventive effect of natural calcitonin on the recurrence thereof (Kissling R O. et al.: Prevention of recurrence of Sudeck's disease with calcitonin., Rev. Chir. Orthop. Reparatrice Appar. Mot., 77, 562-567, 1991. and Marx C. et al.: Preventing recurrence of reflex sympathetic dystrophy in patients requiring an operative intervention at the site of dystrophy after surgery., Clin. Rheumatol., 20, 114-118, 2001.) have been demonstrated clinically. However, for RSD triggered and developed by a stroke, no pharmaceutical agent having a demonstrated safe and sufficient preventive effect has been reported, except for steroid, which is difficult to continuously administer for a long period. According to only one report, the onset of post-stroke RSD was reduced to 8 to 18.5% by restricted loads on the shoulder or paralyzed limbs (Kondo I. et al.: Protocol to prevent shoulder-hand syndrome after stroke., Arch. Phys. Med. Rehabil., 82, 1619-1623, 2001. and Braus D F. et al.: The shoulder-hand syndrome after stroke: a prospective clinical trial., Ann. Neurol., 36, 728-733, 1994.). However, this effect is still insufficient in light of the severity of this disease.

Natural calcitonin is a polypeptide of 32 amino acids secreted from thyroid cells in mammals. The natural calcitonin or a calcitonin derivative suppresses bone resorption by acting on osteoclasts and reduces the serum concentration of calcium. Therefore, these compounds have been used clinically as a therapeutic drug and/or a prophylactic drug for hypercalcemia or osteoporosis. Moreover, the natural calcitonin or the calcitonin derivative has been known widely to have an analgesic effect on a certain pain such as lumbar back ache associated with osteoporosis, cancer pain, or inflammatory pain and has also been reported to have a therapeutic effect on already developed RSD (Wade S. et al.: A critical review of controlled clinical trials for peripheral neuropathic pain and complex regional pain syndromes, PAIN, USA, 73, 123-139, 1997. and Antonio Quatraro: Calcitonin in painful diabetic neuropathy., Lancet, 339, 746-747, 1992.).

On the other hand, with respect to the preventive effect of natural calcitonin on the onset of RSD, there has been reported a preventive effect on the recurrence thereof in patients having an anamnesis of RSD triggered and developed by a trauma or surgical invasion, as described above (Kissling RO. et al.: Prevention of recurrence of Sudeck's disease with calcitonin, Rev. Chir. Orthop. Reparatrice Appar. Mot., 77, 562-567, 1991. and Marx C. et al.: Preventing recurrence of reflex sympathetic dystrophy in patients requiring an operative intervention at the site of dystrophy after surgery., Clin. Rheumatol., 20, 114-118, 2001.). On the other hand, natural calcitonin has been reported to have no preventive effect on the initial onset of RSD in subjects having no anamnesis of RSD after a trauma or surgical invasion (Riou C. et al.: Can algodystrophy be prevented by thyrocalcitonin?, Rev. Chir. Orthop. Reparatrice Appar. Mot., 77, 208-210, 1991.).

Under such circumstances, it has been strongly demanded to develop a novel pharmaceutical drug or a novel therapeutic method having a safe and sufficient preventive effect on RSD developed after stroke.

Thus, an object of the prevent invention is to provide a novel pharmaceutical agent having an excellent preventive effect on post-stroke RSD.

SUMMARY OF THE INVENTION

To attain the object, the present inventor has boldly hypothesized that drug responsiveness differs between the prevention of RSD triggered and developed by a trauma or surgical invasion and the prevention of post-stroke RSD, and has daringly conducted diligent studies on calcitonins that have been reported to have no preventive effect on the initial onset of RSD in subjects having no anamnesis of RSD after a trauma or surgical invasion. As a result, unexpectedly, the present inventor has gained clinical results indicating that calcitonins remarkably prevented the initial onset of RSD.

Calcitonin preparations have been reported to be effective for preventing the recurrence of RSD after a surgical operation or a trauma but ineffective for preventing the initial onset of RSD. Therefore, the prevention of the recurrence of RSD must be differentiated clearly from the prevention of the onset of RSD.

The cause of the onset of RSD has not been elucidated. Thus, it cannot be predicted that drug responsiveness would differ between RSD after a surgical operation or a trauma and post-stroke RSD. In fact, no report states that drug responsiveness to calcitonin preparations as well as other drugs differs between post-stroke RSD and RSD after a surgical operation or a trauma. The prevention of the onset of post-stroke RSD is unpredictable. This is because the pathogenesis of the onset of post-stroke RSD has not been understood, as described above.

Furthermore, the cause of the recurrence of RSD after a surgical operation or a trauma and the characteristics of recurrence-prone patients are unknown. Many RSD pathologies are resistant to therapy in a treatment after the onset of RSD. The characteristics of patients to whom the treatment using calcitonin preparations is effective are unclear.

Thus, it cannot be expected from the prior art that calcitonin preparations are effective for preventing the onset of post-stroke RSD.

Actually, calcitonins have been known to have a therapeutic effect on already developed RSD or a preventive effect on the recurrence of RSD in subjects having an anamnesis of RSD after a trauma or surgical invasion. On the other hand, there was a report that calcitonins have no preventive effect on the initial onset of RSD. Thus, the prior art has rather negated that the use of calcitonins in subjects having no anamnesis of the RSD, particularly subjects having a different history from a trauma or surgical invasion, such as stroke, would bring about a significant effect.

However, surprisingly, the present inventor repetitively administered an eel calcitonin derivative (elcatonin) to, specifically, patients with hemiplegia attributed to stroke, who did not develop RSD on admission. As a result, the present inventor found that the incidence of RSD was suppressed significantly and remarkably until discharge from hospital in this group as compared with an unadministered patient group, and has consequently completed the present invention. In addition, no significant or serious side effect was observed in the patient group to which elcatonin was continuously administered during the test period. Therefore, the present invention proves to be clinically useful and exceedingly revolutionary as an excellently safe agent for preventing the onset of post-stroke RSD, particularly the initial onset of post-stroke RSD.

Specifically, the present invention relates to the following inventions:

(1) an agent for preventing the onset of post-stroke RSD, comprising natural calcitonin or a calcitonin derivative as an active ingredient;

(2) the agent for preventing the onset of RSD according to (1), wherein the natural calcitonin is salmon calcitonin;

(3) the agent for preventing the onset of RSD according to (1), wherein the calcitonin derivative is elcatonin;

(4) the agent for preventing the onset of RSD according to any one of (1) to (3), wherein the administration of the agent is initiated less than 59 days after an attack of stroke and continued until 5 months after the attack;

(5) the agent for preventing the onset of RSD according to any one of (1) to (4), wherein the agent is administered to a patient at Brunnstrom stage III or lower in the upper limb or a finger;

(6) the agent for preventing the onset of RSD according to any one of (1) to (5), wherein the agent for preventing the onset of post-stroke RSD is an agent for preventing the initial onset of post-stroke RSD;

(7) a method for preventing the onset of post-stroke RSD by using natural calcitonin or a calcitonin derivative;

(8) use of natural calcitonin or a calcitonin derivative for preparing an agent for preventing the onset of post-stroke RSD;

(9) a method for preventing the onset of post-stroke reflex sympathetic dystrophy, comprising administering a prophylactically effective amount of natural calcitonin or a calcitonin derivative to a stroke patient;

(10) the method for preventing the onset of post-stroke reflex sympathetic dystrophy according to (9), wherein the natural calcitonin is salmon calcitonin;

(11) the method for preventing the onset of post-stroke reflex sympathetic dystrophy according to (9), wherein the calcitonin derivative is elcatonin;

(12) the method for preventing the onset of post-stroke reflex sympathetic dystrophy according to (9), wherein the administration of a prophylactically effective amount of the natural calcitonin or the calcitonin derivative is initiated less than 59 days after an attack of stroke and continued until 5 months after the attack;

(13) the method for preventing the onset of post-stroke reflex sympathetic dystrophy according to (9), wherein the stroke patient is a patient at Brunnstrom stage III or lower in the upper limb or a finger;

(14) the method for preventing the onset of post-stroke reflex sympathetic dystrophy according to any one of (9) to (13), wherein the onset of post-stroke reflex sympathetic dystrophy is the initial onset of reflex sympathetic dystrophy;

(15) a method for preventing the initial onset of post-stroke reflex sympathetic dystrophy, comprising administering a prophylactically effective amount of natural calcitonin or a calcitonin derivative to a stroke patient at Brunnstrom stage III or lower in the upper limb or a finger, wherein the administration is initiated less than 59 days after an attack of stroke and continued until 5 months after the attack;

(16) the method for preventing the initial onset of post-stroke reflex sympathetic dystrophy according to (15), wherein the natural calcitonin is salmon calcitonin; and

(17) the method for preventing the initial onset of post-stroke reflex sympathetic dystrophy according to (15), wherein the calcitonin derivative is elcatonin.

According to the present invention, RSD developed after stroke can be prevented safely and effectively. According to the present invention, rehabilitation for overcoming paralysis associated with stroke can be performed smoothly. Furthermore, the present invention can contribute to enhancement or improvement in the QOL and ADL of patients.

DETAILED DESCRIPTION OF THE PREFERRED EMBODIMENTS

Hereinafter, the present invention will be described specifically.

Examples of calcitonins useful as an active ingredient in an agent for preventing the onset of post-stroke RSD according to the present invention include a variety of natural calcitonins and calcitonin derivatives.

Examples of the natural calcitonins include chicken calcitonin, eel calcitonin, human calcitonin, salmon calcitonin, and porcine calcitonin, preferably, eel calcitonin and salmon calcitonin (Helv. Chim. Acta (1969), 52 (7), 1789-95), particularly preferably, eel calcitonin. In other cases, salmon calcitonin is preferable.

Examples of the calcitonin derivatives include peptide analogs of natural calcitonin. Specific examples thereof include compounds having chemically modified disulfide bonds at positions 1 and 7 in the structure of the natural calcitonin. More specifically, preferable examples thereof include [ASU1-7] chicken calcitonin, [ASU1-7] eel calcitonin (chemical name described in Japanese Patent Publication (KOKOKU) No. 53-41677: 1-butyric acid-7-(L-2-aminobutyric acid)-26-L-aspartic acid-27-L-valine-29-L-alanine-calcitonin; hereinafter, also referred to as "elcatonin"), particularly preferably, [ASU1-7] eel calcitonin (elcatonin). The calcitonin useful as an active ingredient in the agent for preventing the onset of post-stroke RSD according to the present invention is, particularly preferably, elcatonin or salmon calcitonin, most preferably, elcatonin In other cases, salmon calcitonin is most preferable.

These calcitonins or calcitonin derivatives are exceedingly low toxic. For example, elcatonin was observed to have no lethal toxicity even when it was administered at 13500 or 7400 units/kg (body weight) to mice or rats via each of intravenous, intramuscular, hypodermic and oral routes.

In the present specification, "stroke" is defined as a disease in which brain tissues are damaged or lead to necrosis due to the clogging or rupture of blood vessels distributed to the brain. This disease is also referred to as "cerebrovascular disease" in general. Therefore, in the present specification, both the terms are interchangeably used.

More specifically, the stroke is mainly classified into two disease types, hemorrhagic cerebrovascular disease and ischemic cerebrovascular disease. The hemorrhagic cerebrovascular disease encompasses cerebral hemorrhage and subarachnoid hemorrhage.

On the other hand, examples of the ischemic cerebrovascular disease include cerebral infraction. The cerebral infraction is further classified into two conditions, cerebral thrombosis and cerebral embolism. The cerebral thrombosis refers to a state in which blood vessels in the brain are stenosed due to the progression of cerebral arteriosclerosis, and blood is not supplied to the brain tissues beyond the stenosed site. The cerebral thrombosis is further classified into lacunar infarction, atherothrombotic infarction, etc. Whereas, the cerebral embolism refers to a state in which blood clots or lumps of fat are delivered to the brain and clog blood vessels in the brain. The cerebral embolism is often caused by heart diseases such as valvular disease and myocardial infraction.

The stroke additionally encompasses transient ischemic attack (TIA), hypertensive encephalopathy, and cerebral arteriosclerosis. Diseases corresponding to or classified as stroke have been described in detail in, for example, Domestic and foreign classification history and current classification of cerebrovascular disease (Hirai S., Japanese Journal of Clinical Medicine, 1993 suppl., Strokology in the age of CT and MRI, 7-19, (published by Nippon Rinsho-sha Co., Ltd.)). In the present invention, the disease targeted for administration may be any disease that shows the conditions of stroke defined above in the present specification, and is not limited to particular diseases.

The term "patient(s)" used in the present specification refers to living vertebrates, preferably, humans, diagnosed as having stroke on the basis of diagnostic criteria created by, for example, the Japanese Association for Cerebro-cardiovascular Disease Control or diagnostic criteria set by each medical facility or research facility. The agent for preventing the onset of post-stroke RSD according to the present invention can be administered to these patients.

The term "reflex sympathetic dystrophy (RSD)" used in the present specification refers to a disease defined as RSD according to diagnostic criteria of Veldman et al. in 1993 (Veldman et al., "Signs and Symptoms of reflex sympathetic dystrophy: prospective study of 829 patients", Lancet, 342, 1012-1016, 1993) or as complex regional pain syndrome type I (CRPS-type 1) by the International Association for the Study of Pain in 1994 or as CRPS (not classified into type I and type II) proposed by the International Association for the Study of Pain in 2005.

The RSD was originally defined as a syndrome that is developed after peripheral nerve injury or irrespective of nerve injury, gives rise to excruciatingly abnormal pain in the limbs or the sensitive state to stimuli as a prominent symptom and involves relatively localized autonomic symptoms (Jani W.: Is the reflex sympathetic dystrophy a neurological disease?, In Reflex sympathetic dystrophy, VCH, New York, 1992, pp 9-26). In 1994, the International Association for the Study of Pain proposed CRPS, as a notion concerning disease, and classified RSD involving excruciating causalgia after peripheral nerve injury as CRPS-type 2 and the other conventional RSDs as CRPS-type 1. The diagnostic criteria for CRPS-type 1 provided by the International Association for the Study of Pain include: 1) CRPS-type 1 is a syndrome develops after an inciting noxious event; 2) spontaneous pain, or allodynia/hyperalgesia occurs, is not limited to the territory of a single peripheral nerve, and is disproportionate to the inciting event; 3) there is or has been evidence of edema, skin blood flow abnormality, or abnormal sudomotor activity in the region of the pain occurred since the inciting event; and 4) this diagnosis is excluded by the existence of condition that would otherwise account for the degree of pain and dysfunction. Clinical diagnosis is appropriately conducted according to these criteria (Takahashi A., "Conditions and diagnosis of reflex sympathetic dystrophy", Neurological Medicine, 54, 292-296, 2001).

Examples of diseases classified as CRPS-type 1 or CRPS include shoulder-hand syndrome, minor traumatic dystrophy, and major traumatic dystrophy. The shoulder-hand syndrome is a disease characterized by restrictions on person's movement in a region from the shoulder joint to the hand caused by severe pain, specific swelling of the hand, skin color abnormalities, sensations of burning, etc. As the disease goes on, conditions progress, such as pain in the ipsilateral shoulder and hand, restrictions on person's movement, the swelling of a region from the MP joint to the back of the hand, bone atrophy, allodynia, hyperalgesia, dermal atrophy, reduction in skin temperature, sclerema, atrophy of subcutaneous tissues, joint contracture, and muscular atrophy. These conditions lead to dead limbs in serious cases (Yamaga M. et al., "Shoulder-hand syndrome", Journal of pain and clinical medicine, 4, 115-122, 2004). Shoulder-hand syndrome, minor traumatic dystrophy, and major traumatic dystrophy are also selected as diseases which will be prevented by using the agent for preventing the onset of post-stroke RSD according to the present invention.

For producing the agent for preventing the onset of post-stroke RSD according to the present invention, it is preferred that pharmaceutically acceptable auxiliary ingredients should be added, if needed, to the natural calcitonin or the calcitonin derivative as an active ingredient to prepare a pharmaceutical composition. In this case, the selection of the auxiliary ingredients and the mixing thereof with the active ingredient should be optimized in order to prevent interactions (between the two) that would substantially reduce the pharmacological efficacy of the natural calcitonin or the calcitonin derivative in general use. The pharmaceutically acceptable auxiliary ingredients, of course, must have both high purity and low toxicity sufficient to be administered to patients without any safety problem. Examples of the pharmaceutically acceptable auxiliary ingredients include: sugars such as lactose, glucose, and sucrose; starches such as corn starch and potato starch; cellulose and cellulose derivatives such as sodium carboxymethylcellulose, ethyl cellulose, and cellulose acetate; tragacanth powder; gelatin; talc; stearic acid; magnesium stearate; plant oils such as peanut oil, cottonseed oil, sesame oil, olive oil, corn oil, and theobroma oil; polyols such as propylene glycol, glycerin, sorbitol, mannitol, and polyethylene glycol; agar; alginic acid; tonicity agents; buffers such as phosphate buffer solutions; wetting agents and lubricants such as sodium lauryl sulfate; and coloring agents, flavors, preservatives, stabilizers, antioxidants, antiseptics, and antimicrobial agents.

Examples of the dosage form of the natural calcitonin or the calcitonin derivative of the present invention include injections (or injectable forms), rectal absorption agents, vaginal absorption agents, transnasal absorption agents, transdermal absorption agents, lung absorption agents, and oral absorption agents, and oral administration agents, preferably, injections, transnasal absorption agents, lung absorption agents, and oral administration agents, particularly preferably, injections. In other cases, transdermal absorption agents are preferable. In still other cases, transnasal absorption agents are preferable. In still other cases, lung absorption agents are preferable. In still other cases, oral administration agents are preferable. These dosage forms are not limited by any means.

The natural calcitonin or the calcitonin derivative of the present invention is preferably used in the way of intramuscular, hypodermic, intradermal, or intravenous administration, when administered as an injection. The compound is generally used in the form of a suppository, when administered as a rectal or vaginal absorption agent. The compound is used in the form of a formulation supplemented with an appropriate absorption promoter, when administered as a transnasal or transdermal absorption agent. The compound, when administered as a transdermal absorption agent, is used in the form of a drug-containing adhesive preparation or tape preparation by using an absorption promoter or electric energy or by physically enhancing drug permeability by a scratch in the skin, or is used in the form of an adhesive preparation provided with fine needles on the side attached to the skin, through which the drug seeps, or drug-coated fine needles. The compound is further used in the form of an aerosol composition containing an appropriate dispersant or water and a propellant, when administered as a lung absorption agent. The compound is used in the form of, for example, a sublingual tablet supplemented with an appropriate absorption promoter, when used as an oral absorption agent. Alternatively, the compound is used in the oral form of a liposome or microcapsule formulation, when administered as an oral administration agent.

In order to formulate the natural calcitonin or the calcitonin derivative of the present invention as an injectable form, for example, elcatonin can be dissolved in injection solution (prepared from distilled water) containing a buffer, a tonicity agent, and a pH adjuster in appropriate amounts, and then the mixture can be sterilized though a sterilization filter and dispensed into ampules to prepare the injection. In order to produce the rectal or vaginal absorption agent, for example, elcatonin can be dissolved or dispersed in distilled water or an oil solvent and prepared into a rectal or vaginal injection suppository or a suppository, by use of an appropriately selected absorption promoter having chelating ability, such as sodium pectate or sodium alginate, and an appropriately selected hypertonicity agent such as sodium chloride or glucose (see UK Patent Nos. 2092002 and 2095994).

In order to administer the natural calcitonin or the calcitonin derivative of the present invention as the transnasal absorption agent, for example, elcatonin can be prepared as a liquid preparation or powder supplemented with an absorption promoter such as a water-soluble organic acid (e.g., glucuronic acid, succinic acid, or tartaric acid) (Japanese Patent Application Laying Open (KOKAI) Nos. 63-243033, 63-316737, 1-230530, 2-000111, and 2-104531). Alternatively, the transnasal absorption agent can be obtained by adding an appropriate emulsion to, for example, elcatonin (Japanese Patent Application Laying Open (KOKAI) No. 4-99729). Furthermore, the transnasal preparation can be obtained by using a chitosan-coated nanosphere in order to aseptically charge an aqueous solution containing the natural calcitonin or the calcitonin derivative formulated therein into vials applicable to a mechanical spraying apparatus for intranasal administration illustrated in Japanese Patent Publication (KOKOKU) No. 7-8806.

In order to administer the natural calcitonin or the calcitonin derivative of the present invention as the transdermal absorption agent, the transdermal absorption agent of the natural calcitonin or the calcitonin derivative may be obtained by adding an absorption promoter such as Azone to, for example, salmon calcitonin, for promoting absorption through the skin, as shown in a report (Proceedings of the second annual meeting of the Academy of Pharmaceutical Science and Technology, Japan, p 57-58) or may be obtained by an iontophoretic method (Ann. N.Y. Acad. Sci., 507, 32, 1988). Furthermore, the transdermal absorption agent encompasses the adhesive formulation provided with fine needles on the side attached to the skin, through which the drug seeps, and is exemplified by an adhesive formulation comprising the natural calcitonin or the calcitonin derivative formulated therein disclosed in, for example, National Publication of International Patent Application No. 2004-528900. The transdermal absorption agent is also exemplified by a formulation containing an absorption promoter such as n-octyl-□-D-glucopyranoside and a protease inhibitor such as bestatin and comprising the natural calcitonin or the calcitonin derivative formulated therein, as disclosed in Japanese Patent No. 3054175.

In order to formulate the natural calcitonin or the calcitonin derivative of the present invention as the lung absorption agent, a method may be used, which comprises pulverizing and levigating the natural calcitonin or the calcitonin derivative together with, for example, a dispersant such as Arlacel or Span 80 to prepare an uniform paste, subsequently dispersing this paste into a cooled propellant such as Freon 11 or 12, and then charging this dispersion into containers equipped with valves (Japanese Patent Application Laying Open (KOKAI) No. 60-161924). Other examples of the lung absorption agent include a formulation comprising the natural calcitonin or the calcitonin derivative formulated therein by using a nanosphere having a biodegradable polymer lactic acid-glycolic acid copolymer as a core portion coated with a mucoadhesive polymer chitosan, as disclosed in Japanese Patent Application Laying Open (KOKAI) No. 2000-143533.

In order to formulate the natural calcitonin or the calcitonin derivative of the present invention as the oral absorption agent, for example, ascorbic acids, acidic amino acids, citric acids, unsaturated fatty acids, and salicylic acids can be added alone or in combination of two or more of them to the natural calcitonin or the calcitonin derivative, and an excipient such as glucose, a flavoring agent such as menthol, etc. can be further added thereto to obtain a troche, a sublingual tablet, or a powder (Japanese Patent Application Laying Open (KOKAI) No. 56-140924). Furthermore, the oral administration agent may be prepared from the natural calcitonin or the calcitonin derivative by, for example, a method using a W/O/W emulsion (Endocrinol. Jpn., 23, 493, 1976) or a method using a liposome formulation (Hormone Res., 16, 249, 1982). Another example of the oral administration agent includes a formulation comprising the natural calcitonin or the calcitonin derivative formulated therein by using a caprylic acid derivative as an absorption promoter, as disclosed in U.S. Pat. No. 5,990,166 or by using a chitosan-coated nanosphere, as disclosed in Japanese Patent Application Laying Open (KOKAI) No. 11-116499. Other examples of the oral administration agent include a formulation comprising the natural calcitonin or the calcitonin derivative formulated therein by using a dodecylated chitosan-coated liposome, wherein the preparation can easily adhere to gastrointestinal tract and possesses improved absorbability and sustainability, as disclosed in "Pharmazie, 61 (2), 106-111, 2006". However, the oral administration agent is not limited to these preparations.

The natural calcitonin or the calcitonin derivative of the present invention may be formulated as a continuous administration agent. Continuous administration means an administration method in which a drug is continuously released into the body for a certain period of time or longer. The continuous administration is not limited by an administration route as long as it is systemic administration or local administration to peripheral tissues. Examples thereof include: administration using an instrument such as an infusion pump; manual administration; the hypodermic or intramuscular administration of a sustained-release formulation comprising a biodegradable polymer as a carrier; and the administration of a transnasal absorption agent, a lung absorption agent, or an oral administration agent. In this case, a continuous administration time is preferably 8 hours or longer, more preferably 12 hours or longer, particularly preferably 16 hours or longer.

The dose of the natural calcitonin or the calcitonin derivative contained as an active ingredient in the agent for preventing the onset of post-stroke RSD according to the present invention differs depending on the age, physique, and sex of a patient, the degree of aftereffects including hemiplegia and other symptoms, the specific activity of the calcitonin derivative to be administered, a dosage form, etc. For example, the effective dose of elcatonin used in intramuscular injection is 0.5 to 5000 units/person/day (week), preferably 0.7 to 1000 units/person/day (week), more preferably 1 to 400 units/person/day (week). Therefore, the dose may be adjusted appropriately according to the state of a patient and the form of the prevention agent of the present invention with reference to this range. The number of doses of the natural calcitonin or the calcitonin derivative may be once to twice a day. The natural calcitonin or the calcitonin derivative may be administered every day or once to three times a week. The amount of the natural calcitonin or the calcitonin derivative in the agent is appropriately determined. In sum, a sufficient amount is determined to be equivalent to 0.5 to 5000 units of an elcatonin injection in terms of calcitonin activity per dose. When 200 units of a transnasal absorption agent of salmon calcitonin are administered to a human, as disclosed in, for example, "Calcif. Tissue Int., 46, 5-8, 1990", the serum concentration thereof after administration is 37 pg/mL, which is almost the same concentration as the maximum serum concentration of 20 units of elcatonin intramuscularly administered (Biol. Pharm. Bull., 18 (6), 900, 1995). The specific activity of salmon calcitonin (J Bone Miner Res 17, 1478-1485, 2002) and the specific activity of elcatonin (Current medial care, 20 (12), 2217, 1978) are almost the same. Therefore, the dose of the transnasal absorption agent can be estimated to be approximately 10 times the dose of the injection. Moreover, the dose of an oral administration agent of salmon calcitonin is approximately 60 times the dose of drip infusion in vein, which is estimated from the serum concentration ratio of the oral administration to the drip infusion in vein, as disclosed in, for example, "J Bone Miner Res 17, 1478-1485, 2002". The intramuscular administration of elcatonin requires a dose approximately 1.5 times that of drip infusion in vein for obtaining the maximum serum concentration equal to that in the drip infusion in vein (company data). From these points of view, the dose of the oral administration agent can be estimated to be approximately 90 times the dose of the injection. Thus, the dose of the natural calcitonin or the calcitonin derivative in various dosage forms can be determined on the basis of the serum concentration. Furthermore, an appropriate amount of the natural calcitonin or the calcitonin derivative is dissolved in an appropriate infusion solution such as Solita T-3, and this solution may be subjected to drip infusion in vein over, for example, 1 to several hours or longer. In this case, it is desired that the dose of the natural calcitonin or the calcitonin derivative should be a dose that does not change the serum concentration of calcium. For example, this dose in rat is preferably 0.75 milliunits/kg/week to 75 units/kg/week. In other aspects, a dose of 75 units/kg/week to 400 units/kg/ week is preferable. The dose can be determined for other animal species including humans with reference to this value.

Furthermore, the natural calcitonin or the calcitonin derivative of the present invention may be used for administration in combination with or as a mixture with one or several drugs selected from other agents used as therapeutic agents for RSD in clinical practice, for example, anti-inflammatory analgesics, steroid, low-dose steroid, narcotic analgesics, antidepressants, anticonvulsants, ketamine, neurotrophin, bisphosphonate preparations, sarpogrelate hydrochloride, and mexiletine hydrochloride. Alternatively, the natural calcitonin or the calcitonin derivative may be administered in combination with a variety of nerve block therapies (e.g., a sympathetic or peripheral nerve block), physical therapy and therapeutic exercise, psychotherapy, etc.

Subjects to which the administration of the natural calcitonin or the calcitonin derivative of the present invention is administered are all stroke patients. The incidence of RSD has been reported to be higher in patient with more severe hemiplegia associated with stroke, and so it is particularly desired that the natural calcitonin or the calcitonin derivative of the present invention should be administered to patients with severe hemiplegia. A method for diagnosing the degree of hemiplegia may be, for example, the diagnosis of the degree of hemiplegia in the upper limb or a finger using the Brunnstrom stage. RSD is often developed in severe cases at stage III or lower (e.g., fingers: the voluntary extension of fingers is impossible; the upper limb: flexor-extensor synkinesis appears) determined by the diagnosis. Therefore, it is particularly desired that the natural calcitonin or the calcitonin derivative of the present invention should be administered to patients with severe hemiplegia at stage III or lower determined by the diagnosis. Alternatively, the degree of paralysis may be diagnosed by, for example, SIAS (stroke impairment assessment set). In some cases, it is desired that the natural calcitonin or the calcitonin derivative of the present invention should be administered to patients with severe hemiplegia diagnosed as a SIAS grade of 0 to 2 in a region proximal or distal to the upper limb.

The administration of the natural calcitonin or the calcitonin derivative of the present invention, as shown in Test Example, may be initiated within 59 days after an attack of stroke. It is desired that the administration should be performed, preferably, less than 59 days after the attack, more preferably, within 57 days after the attack, even more preferably, within 55 days after the attack, particularly preferably, within 50 days after the attack, more particularly preferably, within 48 days after the attack. In other cases, the administration is initiated, preferably, less than 30 days after the attack, more preferably, less than 10 days after the attack.

95% of cases developing post-stroke RSD are concentrated on the onset within 5 months after an attack of stroke. Therefore, the administration of the natural calcitonin or the calcitonin derivative of the present invention is continued until 5 months after the attack of stroke in principle. The administration may be continued for a period exceeding 5 months after the attack or may be continued for a shorter period, by the judgment of a clinician according to the state of a patient.

Moreover, the prevention agent of the present invention prevents the onset of post-stroke reflex sympathetic dystrophy and as such, can also prevent various diseases brought by conditions under which the shoulder or hand falls disused, for example, bone atrophy. Such a prevention agent or prevention method is also encompassed within the scope of the present invention.

EXAMPLES

Hereinafter, the present invention will be described in detail with reference to Example and Reference Example. However, the present invention is not intended to be limited to them.

Example 1

Test of Prevention of Onset of Post-Stroke RSD

Test subjects were 33 patients with hemiplegia attributed to cerebrovascular disease (stroke) at Brunnstrom stage III or lower in either the upper limb or a finger on admission. Patients already developing RSD (shoulder-hand syndrome) on admission and patients with pain in the shoulder joint or swollen paralyzed limbs were excluded from the test. To 12 of these 33 test subjects, 20 units of elcatonin (Elcitonin Injection 20S; Asahi-Kasei Pharma; hereinafter, referred to as EL) were intramuscularly administered once a week immediately after admission (EL administration group). On the other hand, 21 test subjects were classified into a rehabilitation alone group (control group) and compared with the EL administration group. Physical therapy and therapeutic exercise, occupational therapy, and the management of the paralyzed limbs were performed thoroughly in all the cases. The details of rehabilitation did not differ between both groups. EL administration was initiated 11 to 59 days after an attack of stroke (25.8 days on average) and continued until 5 months after the attack of stroke. The same observation period was applied to the control group. The test subjects were diagnosed as developing RSD (shoulder-hand syndrome) if they had diffuse pain not localized to the shoulder joint, edema involving skin color changes, skin temperature abnormalities, and range of motion limitations, and the practice of their rehabilitation was restricted. These criteria agreed to Veldman's diagnostic criteria or diagnostic criteria, for CRPS-type 1 provided by the International Association for the Study of Pain.

Activities of daily living (ADL) were evaluated on the basis of the Barthel Index (BI) and the range of motion (ROM) of shoulder joint. The movable range of shoulder joint (also referred to as "shoulder ROM") was regarded as restricted (Shoulder-ROM-restrictions were present.) if either abduction or flexion was restricted in measurement. The test subjects were also examined for sensory impairment, aphasia, and unilateral spatial neglect on admission.

Statistical analysis was conducted with unpaired t-test, Fisher's exact test, or Wilcoxon test, and 5% or lower significance level was regarded as being significant.

As shown in Table 1, no significant difference was observed between the control group and the EL administration group in any of items of an age, a male-female ratio, a primary disease type, a paralysis stage, the presence or absence of aphasia, the presence or absence of unilateral spatial neglect, the degree of sensory impairment, the presence or absence of restrictions of shoulder joints, and the presence or absence of shoulder pain. Furthermore, no significant difference was observed between them in BI on admission.

TABLE 1

Background of Patients

|  |  | Control group | EL preventive administration group | P-value |
|---|---|---|---|---|
| BrST | I | 8 | 2 | 0.2627 |
|  | II | 7 | 5 |  |
|  | III | 6 | 5 |  |
| Male-female ratio | Male | 15 | 9 | 1 |
|  | Female | 6 | 3 |  |
| Primary disease | Cerebral infarction | 12 | 8 | 1 |
|  | Cerebral hemorrhage | 8 | 4 |  |
|  | SAH | 1 | 0 |  |
| Aphasia | Present | 7 | 2 | 0.4293 |
|  | Absent | 14 | 10 |  |
| Spatial neglect | Present | 8 | 5 | 1 |
|  | Absent | 13 | 7 |  |
| Sensory impairment | Absent | 1 | 0 | 0.47 |
|  | Mild | 3 | 5 |  |
|  | Moderate | 9 | 3 |  |
|  | Severe | 8 | 4 |  |
| Shoulder ROM Restrictions | Present | 0 | 2 | 0.125 |
|  | Absent | 21 | 10 |  |
| BI | Median | 15 | 25 | 0.7340 |
|  | (Average ± SE) | (22.6 ± 4.5) | (28.8 ± 8.1) |  |
| Age | Average ± SE | 68.0 ± 2.6 | 70.5 ± 2.4 | 0.2288 |

BrST: Brunnstrom stage
BI: Barthel index
(Unit: the number of persons except for BI and age)

Next, the number of test subjects developing RSD (shoulder-hand syndrome) after the test is shown in Table 2. In the control group, 11 of the 21 cases (52.4%) developed RSD. On the other hand, in the EL preventive administration group, 1 of the 12 cases (8.3%) developed RSD. Thus, the number of test subjects (the number of persons) developing RSD was significantly low in the EL preventive administration group as compared with the control group. When these two incidences were converted to incidences in all patients with hemiplegia attributed to cerebrovascular disease (stroke) in the facility, as in various reports, the incidences were approximately 8.7% in the control group and approximately 1.3% in the EL administration group. In further detailed analysis, administration to the 1 case developing RSD in the EL preventive administration group was initiated 59 days after stroke. In the other cases, that is, when EL administration was initiated within 48 days after stroke, the incidence of RSD was 0%, demonstrating a remarkable preventive effect from RSD.

In the process of the onset of RSD, diffuse pain, edema involving skin color changes, and skin temperature abnormalities occur almost simultaneously, and range of motion restrictions occur slightly later than these symptoms. However, no case developed each symptom alone.

TABLE 2

The Number of Test Subjects Developing Post-Stroke RSD

|  | Control group | EL preventive administration group | p-value |
|---|---|---|---|
| Developed | 11 | 1 | 0.022 |
| Not developed | 10 | 11 |  |

Reference Example 1

Test of Treatment of Post-Stroke RSD

EL was administered after the onset of RSD (shoulder-hand syndrome) in the same use and dose as in Example 1 to 11 patients with hemiplegia attributed to cerebrovascular disease (stroke) at Brunnstrom stage III or lower in either the upper limb or a finger on admission, who developed RSD (shoulder-hand syndrome). These patients were classified into a therapeutic administration group. On the other hand, the EL administration group of Example 1 was compared as a control (preventive administration group) with the therapeutic administration group. An observation period did not differ between both the groups. As a result, in the therapeutic administration group, diffuse pain, shoulder joint pain and the progression of range of motion restrictions was slightly suppressed. However, the symptoms of RSD could not be suppressed completely in any case (Table 3). Moreover, the Barthel index at the completion of EL administration was significantly low in the therapeutic administration group as compared with the preventive administration group (Table 3).

TABLE 3

Comparison Between Therapeutic Administration and Preventive Administration of Elcatonin (at Completion of Administration)

|  |  | Therapeutic administration group | Preventive administration group | p-value |
|---|---|---|---|---|
| RSD | The number of | 11 | 1 | <0.0001 |
| No RSD | persons | 0 | 11 |  |
| Barthel index | Median | 25 | 72.5 | 0.0448 |
|  | Average ± SE | 31.8 ± 7.8 | 60.8 ± 9.3 |  |

Thus, it was shown that EL administration to severe paralysis patients with hemiplegia after cerebrovascular disease (stroke) at Brunnstrom stage III or lower in either the upper limb or a finger has a remarkably excellent preventive effect provided by administration before the onset of RSD rather than a therapeutic effect (improvement effect) provided by administration after the onset of RSD.

The natural calcitonin or the calcitonin derivative of the present invention is exceedingly effective in the prevention of the onset of reflex sympathetic dystrophy (RSD), particularly, the initial onset of post-stroke RSD, and so it can be utilized in the field of pharmaceutical industry for providing a pharmaceutical agent used in these applications.

What is claimed is:

1. A method for preventing an initial onset of post-stroke shoulder-hand syndrome, comprising administering a prophylactically effective amount of natural calcitonin or a calcitonin derivative to a stroke patient, wherein said natural calcitonin is selected from the group consisting of chicken calcitonin, eel calcitonin, human calcitonin, salmon calcitonin and porcine calcitonin, and wherein said calcitonin derivative is a compound having chemically modified disulfide bonds at positions 1 and 7 in the structure of aforementioned natural calcitonin.

2. The method for preventing an initial onset of post-stroke shoulder-hand syndrome according to claim 1, wherein the calcitonin is salmon calcitonin or a derivative thereof.

3. The method for preventing an initial onset of post-stroke shoulder-hand syndrome according to claim 1, wherein the calcitonin is eel calcitonin or a derivative thereof.

4. The method for preventing an initial onset of post-stroke shoulder-hand syndrome according to claim 1, wherein the administration of a prophylactically effective amount of the natural calcitonin or the calcitonin derivative is initiated less than 59 days after an attack of stroke and continued until 5 months after the attack.

5. The method for preventing an initial onset of post-stroke shoulder-hand syndrome according to claim 1, wherein the stroke patient is a patient at Brunnstrom stage III or lower in the upper limb or a finger.

6. The method for preventing an initial onset of post-stroke shoulder-hand syndrome according to claim 1, wherein the calcitonin is salmon calcitonin.

7. The method for preventing an initial onset of post-stroke shoulder-hand syndrome according to claim 1, wherein the calcitonin is a derivative of eel calcitonin.

8. The method for preventing an initial onset of post-stroke shoulder-hand syndrome according to claim 7, wherein the derivative of eel calcitonin is elcatonin.

9. A method for preventing an initial onset of post-stroke shoulder-hand syndrome, comprising administering a prophylactically effective amount of natural calcitonin or a calcitonin derivative to a stroke patient at Brunnstrom stage III or lower in the upper limb or a finger, wherein the administration is initiated less than 59 days after an attack of stroke and continued until 5 months after the attack, wherein said natural calcitonin is selected from the group consisting of chicken calcitonin, eel calcitonin, human calcitonin, salmon calcitonin and porcine calcitonin, and wherein said calcitonin derivative is a compound having chemically modified disulfide bonds at positions 1 and 7 in the structure of aforementioned natural calcitonin.

10. The method for preventing an initial onset of post-stroke shoulder-hand syndrome according to claim 9, wherein the calcitonin is salmon calcitonin or a derivative thereof.

11. The method for preventing an initial onset of post-stroke shoulder-hand syndrome according to claim 9, wherein the calcitonin is eel calcitonin or a derivative thereof.

12. The method for preventing an initial onset of post-stroke shoulder-hand syndrome according to claim 9, wherein the calcitonin is salmon calcitonin.

13. The method for preventing an initial onset of post-stroke shoulder-hand syndrome according to claim 9, wherein the calcitonin is a derivative of eel calcitonin.

14. The method for preventing an initial onset of post-stroke shoulder-hand syndrome according to claim 13, wherein the derivative of eel calcitonin is elcatonin.

* * * * *